(12) United States Patent
Tsai et al.

(10) Patent No.: US 9,504,540 B2
(45) Date of Patent: Nov. 29, 2016

(54) DENTAL IMPLANT WITH POSITIONING MARKER AND INDEX PORTIONS

(71) Applicant: METAL INDUSTRIES RESEARCH & DEVELOPMENT CENTRE, Kaohsiung (TW)

(72) Inventors: Tung-Lin Tsai, Kaohsiung (TW); Bo-Wei Pan, Kaohsiung (TW); Yi-Chin Chen, Kaohsiung (TW); Pei-Hua Wang, Kaohsiung (TW)

(73) Assignee: Metal Industries Research & Development Centre, Kaohsiung (TW)

(*) Notice: Subject to any disclaimer, the term of this patent is extended or adjusted under 35 U.S.C. 154(b) by 249 days.

(21) Appl. No.: 14/467,096

(22) Filed: Aug. 25, 2014

(65) Prior Publication Data

US 2016/0008103 A1    Jan. 14, 2016

(30) Foreign Application Priority Data

Jul. 10, 2014    (TW) .............................. 103123823 A

(51) Int. Cl.
*A61C 8/00* (2006.01)

(52) U.S. Cl.
CPC ............. *A61C 8/0022* (2013.01); *A61C 8/006* (2013.01); *A61C 8/0059* (2013.01); *A61C 8/0066* (2013.01); *A61C 8/0068* (2013.01); *A61C 8/0069* (2013.01)

(58) Field of Classification Search
CPC ...... A61C 8/00; A61C 8/0028; A61C 13/08; A61C 8/022; A61C 8/0069
See application file for complete search history.

(56) References Cited

U.S. PATENT DOCUMENTS

| | | | |
|---|---|---|---|
| 5,468,149 A | 11/1995 | D'Alise | |
| 5,989,028 A | 11/1999 | Niznick | |
| 6,287,117 B1 | 9/2001 | Niznick | |
| 2004/0101808 A1* | 5/2004 | Porter | A61C 8/0001 433/173 |
| 2006/0194170 A1* | 8/2006 | Wohrle | A61C 8/0018 433/173 |
| 2007/0190489 A1* | 8/2007 | Riley | A61C 13/0001 433/173 |
| 2014/0302458 A1* | 10/2014 | Towse | A61C 8/009 433/174 |

* cited by examiner

*Primary Examiner* — Jason-Dennis Stewart
(74) *Attorney, Agent, or Firm* — Alan D. Kamrath; Kamrath IP Lawfirm, P.A.

(57) ABSTRACT

A dental prosthesis includes an implanting end, a coupling end, and a screw portion between the implanting end and the coupling end. The dental prosthesis further includes a positioning marker portion located adjacent to the coupling end of the dental prosthesis. The dental prosthesis can be precisely located in an alveolar bone of a patient. A dental implant includes the dental prosthesis and an abutment. The abutment includes a prosthesis coupling end. The prosthesis coupling end of the abutment is coupled to the coupling end of the dental prosthesis.

11 Claims, 5 Drawing Sheets

DENTAL IMPLANT WITH POSITIONING MARKER AND INDEX PORTIONS

BACKGROUND OF THE INVENTION

1. Field of the Invention

The present invention relates to a dental prosthesis and, more particularly, to a dental prosthesis that can be precisely located in an alveolar bone. The present invention also relates to a dental implant including the dental prosthesis.

2. Description of the Related Art

Tooth implantation includes implanting a dental implant into an alveolar bone in the location of a missing tooth. After the dental implant has tightly engaged with the alveolar bone, a ceramic crown is mounted to a top face of the dental implant. Thus, the artificial tooth of the dental implantation is firmer than conventional artificial teeth. Consumers prefer dental implantation because there is no trace of the artificial tooth in appearance.

FIG. 1 shows a conventional dental implant 9 including a dental prosthesis 91 and an abutment 92. The abutment 92 is coupled to an end of the dental prosthesis 91 and includes a contour portion 921. A practitioner places the dental prosthesis 91 into an alveolar bone of a patient during surgery, with the most suitable side of the dental prosthesis 91 facing an outer side of a tooth (namely, the outer side of a ceramic crown C to be fixedly mounted in the future). After the dental prosthesis 91 and the alveolar bone have tightly engaged with each other, a second surgery is carried out to mount the abutment 92 onto an end of the dental prosthesis 91, and a ceramic crown C is then fixedly mounted to the abutment 92. The gum G of the patient will grow along the outline of the contour portion 921 to form a substantially m-shaped curve.

However, since the dental prosthesis 91 has tightly engaged with the alveolar bone during the second surgery, in a case that the dental prosthesis 91 does not face the outer side of the tooth with its most suitable side (such as in the case of an angle deviation), the practitioner will not be able to conduct minor adjustment while coupling the abutment 92 with the dental prosthesis 91. Thus, the above m-shaped curve could not be formed when the gum G of the patient grows along the contour portion 921, leading to degradation in the overall visual impression of the appearance.

Thus, a need exists for a dental prosthesis and a dental implant including the dental prosthesis to solve the above disadvantages.

SUMMARY OF THE INVENTION

An objective of the present invention is to provide a dental prosthesis that can be precisely positioned in an alveolar bone of a patient.

Another objective of the present invention is to provide a dental implant that can be precisely positioned in an alveolar bone of a patient to improve the visual impression of the appearance after tooth implantation.

The present invention fulfills the above objectives by providing a dental prosthesis including an implanting end, a coupling end, and a screw portion between the implanting end and the coupling end. The dental prosthesis further includes a positioning marker portion located adjacent to the coupling end of the dental prosthesis.

The dental prosthesis can further include an engagement groove having an opening. The opening faces the coupling end of the dental prosthesis.

The dental prosthesis can further include a toothed portion located on an inner periphery of the engagement groove. The toothed portion includes a plurality of continuous cavities. In an example, the plurality of continuous cavities includes twelve continuous cavities.

The dental prosthesis can further include a conical portion on the inner periphery of the engagement groove. The conical portion is located between the toothed portion and the opening. In an example, the conical portion has a conicity in a range of 8°-22°.

The dental prosthesis can further include an adhesion layer formed on a surface of the conical portion. In an example, the adhesion layer is also formed on a surface of the toothed portion.

A dental implant according to the present invention includes a dental prosthesis and an abutment. The dental prosthesis includes an implanting end, a coupling end, and a screw portion between the implanting end and the coupling end. The dental prosthesis further includes a positioning marker portion located adjacent to the coupling end of the dental prosthesis. The abutment includes a prosthesis coupling end. The prosthesis coupling end of the abutment is coupled to the coupling end of the dental prosthesis.

The abutment can further include a contour portion. The contour portion is exposed when the abutment is coupled to the dental prosthesis.

The abutment can further include a positioning index portion. The positioning index portion is aligned with the positioning marker portion. In an example, the positioning index portion is located on an outer periphery of the contour portion.

The abutment can further include a coupling portion located on the prosthesis coupling end. The coupling portion is coupled to the toothed portion of the dental prosthesis.

The abutment can further include an abutting portion located between the coupling portion and the contour portion. The abutting portion is coupled to the conical portion of the dental prosthesis.

The abutment can further include an adhesion layer formed on an outer periphery of the abutting portion. In an example, the adhesion layer of the abutment is also formed on an outer periphery of the coupling portion.

The dental prosthesis according to the present invention includes the positioning marker portion to provide assistance while the practitioner is implanting the dental prosthesis into an alveolar bone such that the dental prosthesis faces the outer side of the tooth with its most suitable side, increasing the positioning precision of the dental prosthesis.

Furthermore, the dental implant according to the present invention includes the above dental prosthesis. In addition to precisely locating the dental prosthesis in the implantation location of the alveolar bone in advance, the abutment can precisely be aligned with the dental prosthesis by the alignment between the positioning index portion and the positioning marker portion, improving the overall visual impression of the oral cavity of the patient.

The present invention will become clearer in light of the following detailed description of illustrative embodiments of this invention described in connection with the drawings.

DETAILED DESCRIPTION OF THE INVENTION

Figure 1:
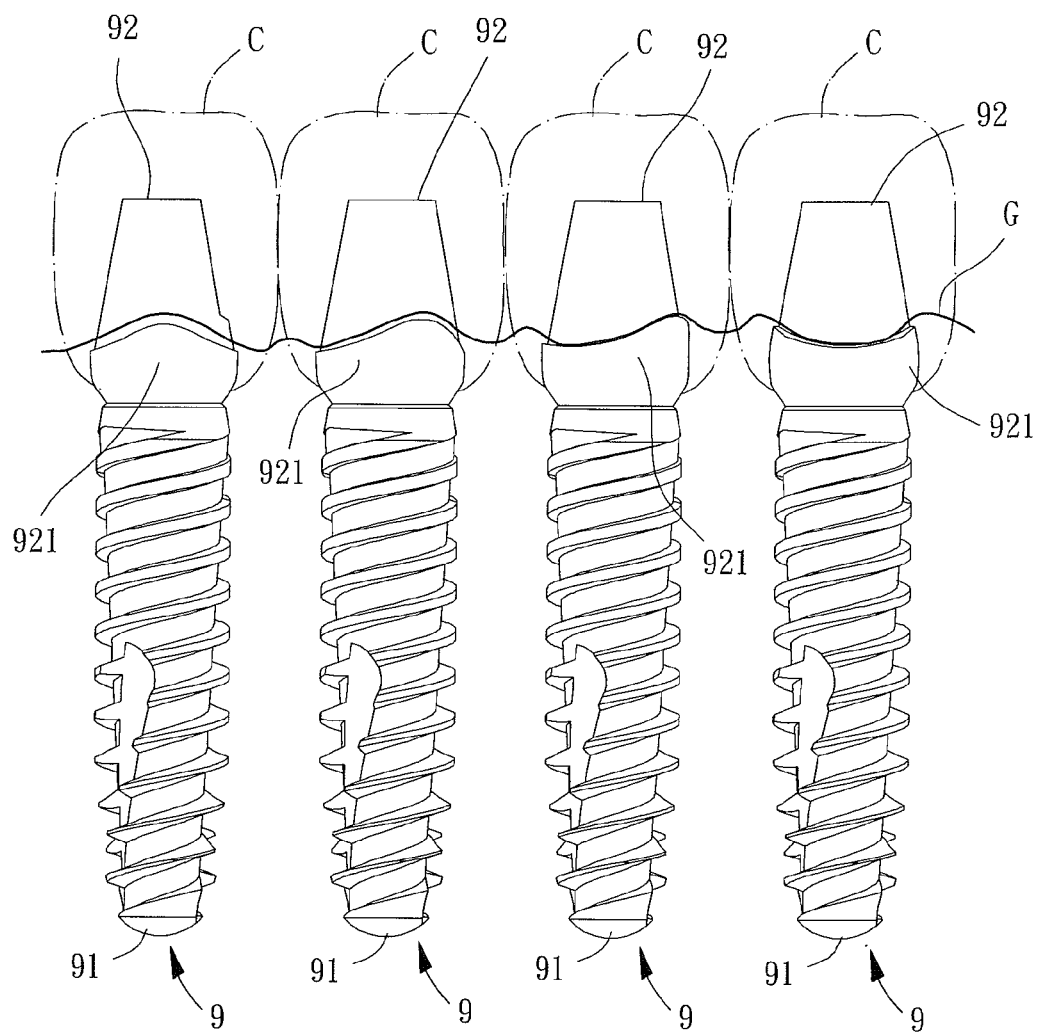
FIG. 1 is a schematic view illustrating a plurality of conventional dental implants implanted into a gum.
Figure 2:
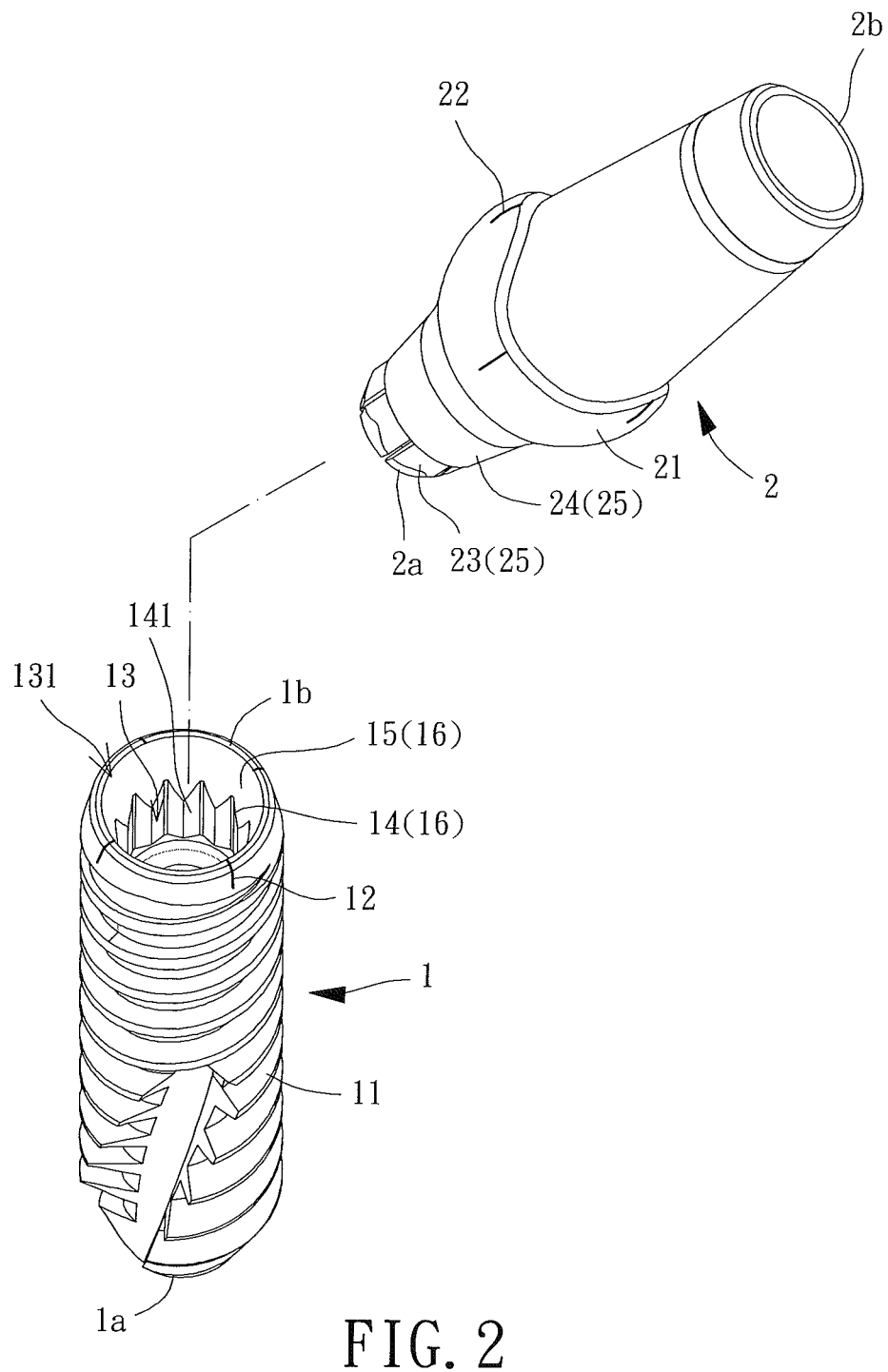
FIG. 2 is an exploded, perspective view of a dental implant according to the present invention.

With reference to FIG. 2, a dental implant according to the present invention includes a dental prosthesis 1 and an abutment 2. An end of the abutment 2 is coupled to the dental prosthesis 1. A ceramic crown C (FIG. 7) is adapted to be mounted to the other end of the abutment 2. The dental implant can be made of a medical-grade material (such as a ceramic material including titanium or zirconium oxide). The specific high bio-compatibility of the medical-grade material can reduce the tooth sensitivity of the patient after implantation of the dental implant.

The dental prosthesis 1 includes an implanting end 1a and a coupling end 1b opposite to the implanting end 1a. The implanting end 1a is adapted to be implanted into an alveolar bone of a patient at a location of a missing tooth. The dental prosthesis 1 further includes a screw portion 11 between the implanting end 1a and the coupling end 1b. The screw portion 11 permits smooth implantation of the dental prosthesis 1 into the alveolar bone and permits the dental prosthesis 1 to be securely positioned in the alveolar bone.

The dental prosthesis 1 can further include a positioning marker portion 12. The positioning marker portion 12 allows a practitioner to define the optimal orientation of the dental prosthesis 1, such that the dental prosthesis 1 faces the outer side of the tooth with its most suitable side when the dental prosthesis 1 is implanted into the alveolar bone. Preferably, the optimal orientation of the dental prosthesis 1 is defined as 0°. Furthermore, the positioning marker portion 12 can be provided in a plurality of angular locations such that the practitioner can easily identify the optimal orientation (e.g., the positioning marker portion 12 can be provided in 0°, 90°, 180°, and 270° locations). Preferably, the positioning marker portion 12 is located adjacent to the coupling end 1b of the dental prosthesis 1 such that the positioning marker portion 12 can still easily be seen to precisely locate the implantation position of the dental prosthesis 1 by the positioning marker portion 12.

Figure 3:
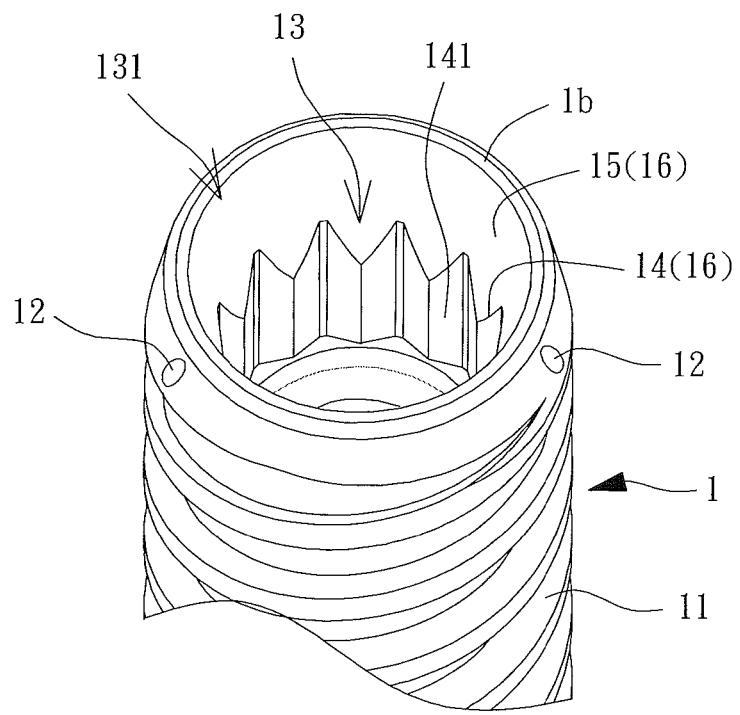
FIG. 3 is a partial, perspective view of a dental prosthesis of the dental implant according to the present invention.
Figure 4:
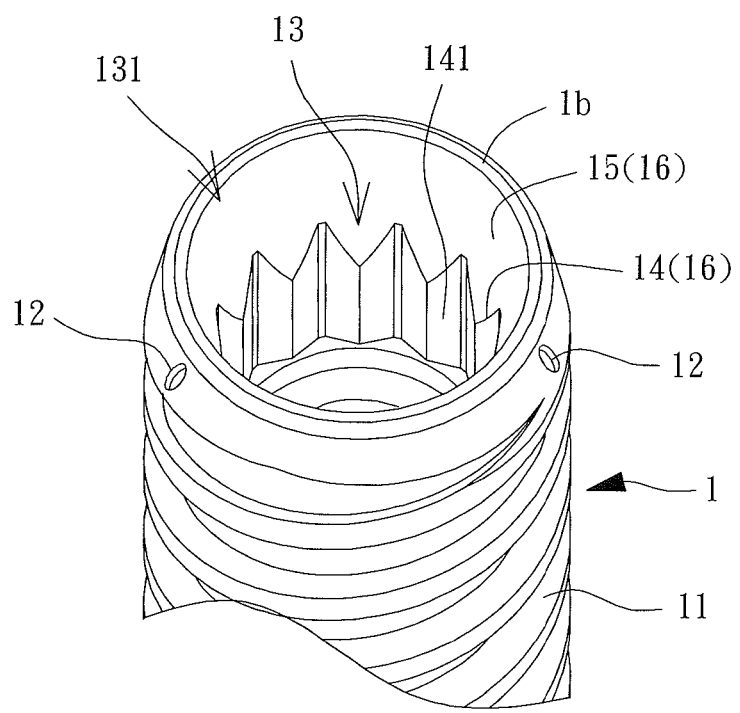
FIG. 4 is another partial, perspective view of the dental prosthesis of the dental implant according to the present invention.

With reference to FIGS. 2-4, the positioning marker portion 12 can be of any structure recessed in, flush with, or protruding from the surface of the dental prosthesis 1. As an example, the positioning marker portion 12 can be a nick carved on the surface of the dental prosthesis 1, a mark printed on the surface of the dental prosthesis 1, a label adhered to the surface of the dental prosthesis 1, or a ridge coupled to the surface of the dental prosthesis 1. In another example, the positioning marker portion 12 can be a protrusion on or a recession in the surface of the dental prosthesis 1. Furthermore, the positioning marker portion 12 can be formed by laser carving such that the dental prosthesis 1 can still have a smooth surface to reduce discomfort of the patient after implantation of the dental prosthesis 1. Alternatively, in a case that the dental prosthesis 1 is made of a titanium alloy, electroplating can be used to form an oxide layer of a desired thickness on the surface of the dental prosthesis 1. The oxide layer can serve as the positioning marker portion 12. In this case, the positioning marker portion 12 can have different colors.

Figures 5, 6:
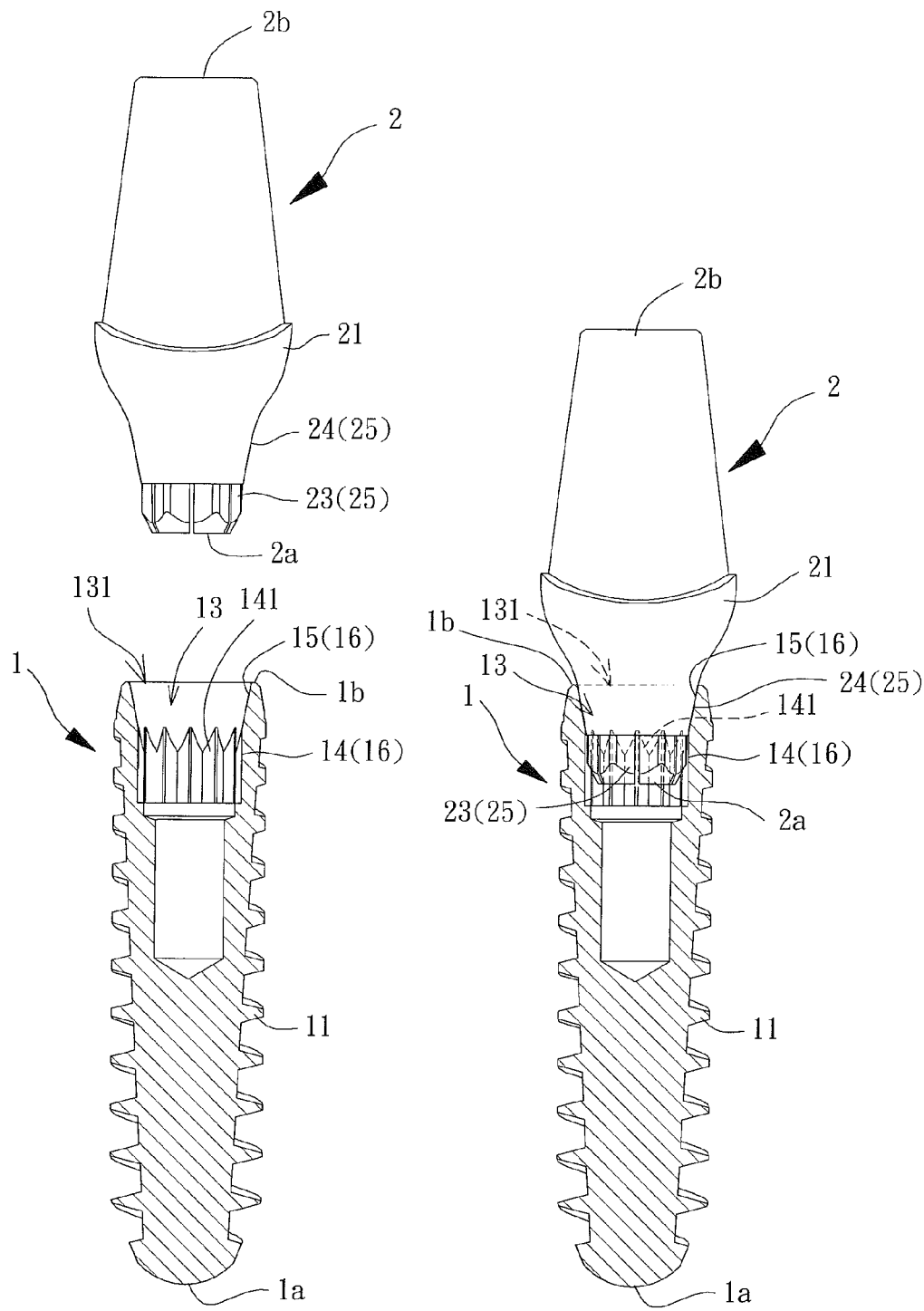
FIG. 5 is an exploded, cross sectional view of the dental implant according to the present invention.
FIG. 6 is a cross sectional view of the dental implant according to the present invention after assembly.

With reference to FIGS. 2 and 5, the dental prosthesis 1 can further include an engagement groove 13 in the coupling end 1b. The engagement groove 13 has an opening 131 facing the coupling end 1b. Thus, the abutment 2 can extend into the engagement groove 13 for coupling with the dental prosthesis 1.

Furthermore, the dental prosthesis 1 includes a toothed portion 14 located on an inner periphery of the engagement groove 13. The toothed portion 14 includes a plurality of continuous cavities 141. The number of the cavities 141 can be varied according to the outline of the abutment 2. In this embodiment, the cavities 141 include twelve (12) continuous cavities 141. Thus, the positioning marker portion 12 can be coupled to the dental prosthesis 1 in one of many angular positions.

The dental prosthesis 1 can further include a conical portion 15. The conical portion 15 is also provided on the inner periphery of the engagement groove 13. Furthermore, the conical portion 15 is located between the toothed portion 14 and the opening 131. Preferably, the conical portion 15 has a conicity in a range of 8°-22°. Thus, when the dental prosthesis 1 couples with the abutment 2, the conical portion 15 presents a vacuum state by the conicity, effectively preventing falling of the abutment 2.

To improve the coupling tightness between the dental prosthesis 1 and the abutment 2, the dental prosthesis 1 can further include an adhesion layer 16. The adhesion layer 16 can be formed on a surface of the conical portion 15. The adhesion layer 16 can also be formed on a surface of the toothed portion 14. Alternatively, the adhesion layer 16 can cover the whole inner periphery of the engagement groove 13. The adhesion layer 16 can be made of a metal having excellent ductility (such as gold or silver). Thus, when the abutment 2 is coupled in the engagement groove 13, the ductility of the adhesion layer 16 provides a cold welding effect to increase the vacuum degree of the coupling area, further preventing the abutment 2 from falling from the dental prosthesis 1.

Figure 7:
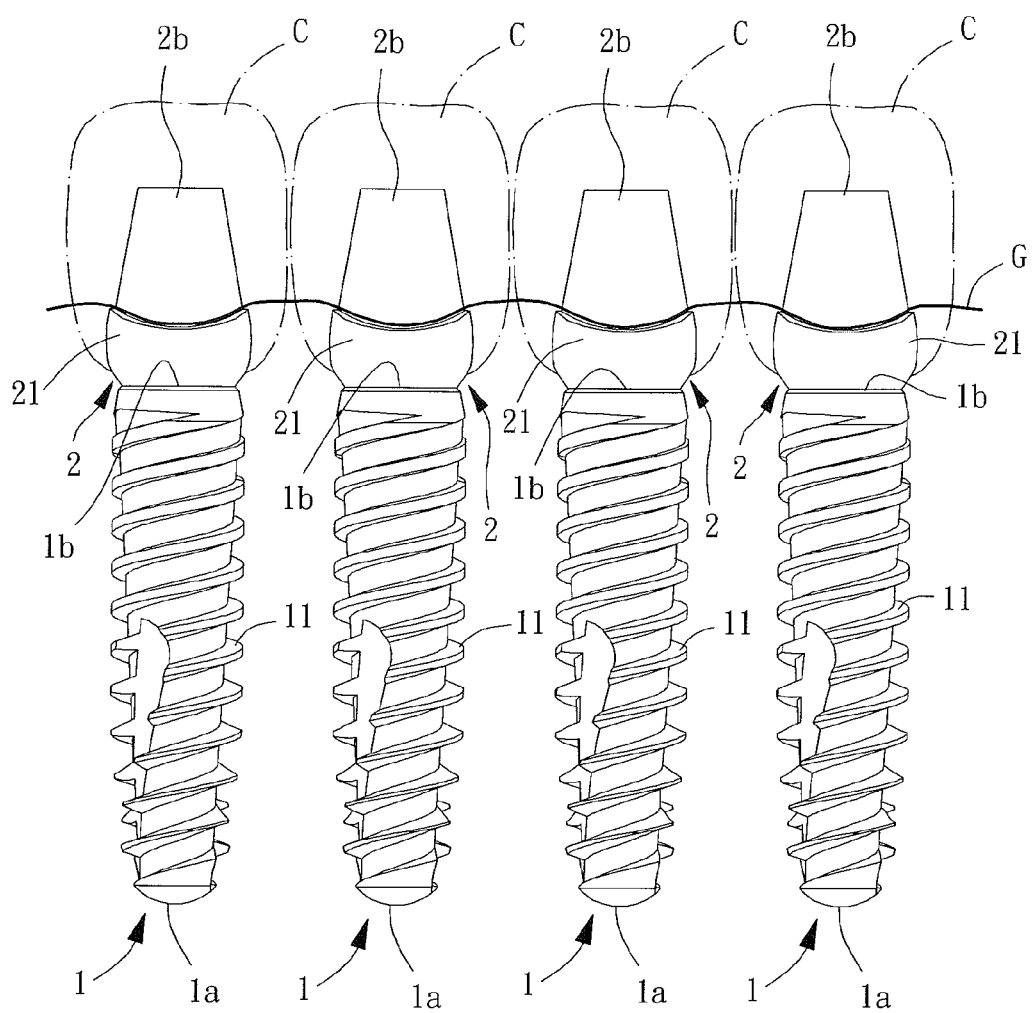
FIG. 7 is a schematic view illustrating a plurality of dental implants according to the present invention implanted into a gum.

The abutment 2 includes a prosthesis coupling end 2a and a crown coupling end 2b opposite to the prosthesis coupling end 2a. The prosthesis coupling end 2a is coupled to the coupling end 1b of the dental prosthesis 1. The crown coupling end 2b is adapted to couple with a ceramic crown C (FIG. 7). The abutment 2 further includes a contour portion 21. The contour portion 21 is exposed when the prosthesis coupling end 2a of the abutment 2 is coupled to the dental prosthesis 1. The gum G of a patient can grow along the contour portion 21.

The abutment can further include a positioning index portion. The positioning index portion 22 can be aligned with the positioning marker portion 12 of the dental prosthesis 1. Thus, when the abutment 2 is coupled to the dental prosthesis 1, the abutment 2 can be precisely located in an exact position relative to the dental prosthesis 1 by the alignment between the positioning index portion 22 and the positioning marker portion 12. Preferably, the positioning index portion 22 is located on an outer periphery of the contour portion 21. Similar to the positioning marker portion 12, the positioning index portion 22 can be of any structure recessed in, flush with, or protruding from the surface of the abutment 2 and can be formed by laser carving or electroplating. Redundant description is not required.

The abutment 2 further includes a coupling portion 23 and an abutting portion 24. The coupling portion 23 is located on the prosthesis coupling end 2a. The abutting portion 24 is located between the coupling portion 23 and the contour portion 21. The coupling portion 23 corresponds to the number of the cavities 141 of the toothed portion 14 of the dental prosthesis 1. The coupling portion 23 has non-circular cross sections. In this embodiment, the coupling portion 23 has hexagonal cross sections such that the coupling portion 23 includes a peripheral face having six faces to proceed with coupling with the dental prosthesis 1 in different angular positions. Furthermore, the abutting portion 24 tapers from the contour portion 21 towards the coupling portion 23 such that an end of the abutting portion 24 adjacent to the coupling portion 23 has the minimal cross sectional area. The abutting portion 24 is coupled to the conical portion 15 of the dental prosthesis 1.

Furthermore, the abutment 2 can further include an adhesion layer 25. The adhesion layer 25 can be made of a metal having excellent ductility (such as gold or silver). Preferably, the adhesion layer 25 is formed on an outer periphery of the abutting portion 24. Alternatively, the adhesion layer 25 can be formed on both of the outer periphery of the abutting portion 24 and an outer periphery of the coupling portion 23. When the prosthesis coupling end 2a of the abutment 2 extends into and couples with the engagement groove 13, the adhesion layer 16 and the adhesion layer 25 together provide a cold welding effect such that the adhesion layer 16 and the adhesion layer 25 can engage with each other more tightly. However, the adhesion layer 16 does not have to function together with the adhesion layer 25. Responsive to the conditions of the oral cavity of the patient, the dental prosthesis 1 does not have to include the adhesion layer 16 or the abutment 2 does not have to include the adhesion layer 25.

Furthermore, the dental implant can further include a fastener (not shown) to provide stable coupling between the dental prosthesis 1 and the abutment 2, which can be appreciated by one having ordinary skill in the art. Detailed description is not required.

With reference to FIGS. 6 and 7, the practitioner can implant the dental prosthesis 1 into an alveolar bone of a patient by the implanting end 1a. Furthermore, the positioning marker portion 12 provides the optimal orientation for subsequent coupling with the abutment 2. After the prosthesis coupling end 2a extends into and couples with the engagement groove 13, the contour portion 21 of the abutment 2 provides the best contour for growth of the gum G. After the positioning index portion 22 of the abutment 2 has aligned with the positioning marker portion 12, it is assured that the abutment 2 is precisely located on the coupling end 1b of the dental prosthesis 1. Then, after mounting a ceramic crown C to the abutment 2, the gum G of the patient will grow along the contour portion 21 of the abutment 2, and the procedures of tooth implantation surgery are completed. By the alignment between the positioning marker portion 12 and the positioning index portion 22, degradation in the overall visual impression of the appearance resulting from positioning deviation between the dental prosthesis 1 and the abutment 2 can be avoided.

Furthermore, by providing the toothed portion 14 on the inner periphery of the engagement groove 13, the abutment 2 can have many angular coupling positions relative to the dental prosthesis 1 while coupling the abutment 2 with the dental prosthesis 1. This permits minor adjustment of the abutment 2 relative to the dental prosthesis 1 while improving the overall visual impression of the appearance.

Furthermore, by providing the conical portion 15 on the inner periphery of the engagement groove 13, the contact between the dental prosthesis 1 and the abutment 2 is in a vacuum state when the dental prosthesis 1 couples with the abutment 2, increasing the coupling stability between the dental prosthesis 1 and the abutment 2. Furthermore, due to the ductility of the adhesion layer 16 on the conical portion 15 (or covering the whole inner periphery of the engagement groove 13) and the ductility of the adhesion layer 25 on the outer periphery of the abutting portion 24 (or on the outer periphery of the abutting portion 24 and the outer periphery of the coupling portion 23), the coupling stability between the dental prosthesis 1 and the abutment 2 can be improved to prevent falling of the abutment 2.

In view of the foregoing, the dental prosthesis 1 according to the present invention includes the positioning marker portion 12 to provide assistance while the practitioner is implanting the dental prosthesis 1 into an alveolar bone such that the dental prosthesis 1 faces the outer side of the tooth with its most suitable side, increasing the positioning precision of the dental prosthesis 1.

Furthermore, the dental implant according to the present invention includes the above dental prosthesis 1. In addition to precisely locating the dental prosthesis 1 in the implantation location of the alveolar bone in advance, the abutment 2 can precisely be aligned with the dental prosthesis 1 by the alignment between the positioning index portion 22 and the positioning marker portion 12, improving the overall visual impression of the oral cavity of the patient.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A dental implant comprising:
   a dental prosthesis including an implanting end, a coupling end, and a screw portion between the implanting end and the coupling end, with the dental prosthesis further including a positioning marker portion located adjacent to the coupling end of the dental prosthesis; and
   an abutment including a prosthesis coupling end and a positioning index portion, with the prosthesis coupling end of the abutment coupled to the coupling end of the dental prosthesis, and with the positioning index portion aligned with the positioning marker portion.

2. The dental implant as claimed in claim 1, with the abutment further including a contour portion, wherein the contour portion is exposed when the abutment is coupled to the dental prosthesis.

3. The dental implant as claimed in claim 1, with the positioning index portion located on an outer periphery of the contour portion.

4. The dental implant as claimed in claim 1, with the abutment further including a coupling portion located on the prosthesis coupling end, and with the coupling portion coupled to a toothed portion of the dental prosthesis.

5. The dental implant as claimed in claim 4, with the abutment further including an abutting portion located between the coupling portion and the contour portion, and with the abutting portion coupled to a conical portion of the dental prosthesis.

6. The dental implant as claimed in claim 5, with the abutment further including an adhesion layer, with the adhesion layer of the abutment formed on an outer periphery of the abutting portion.

7. The dental implant as claimed in claim 6, with the adhesion layer of the abutment also formed on an outer periphery of the coupling portion.

8. The dental implant as claimed in claim 6, with the dental prosthesis further including an engagement groove having an opening and an inner periphery, with the opening facing the coupling end of the dental prosthesis, with the dental prosthesis further including a toothed portion located on the inner periphery of with the engagement groove, and with the toothed portion including a plurality of continuous cavities.

9. The dental implant as claimed in claim 8, with the dental prosthesis further including a conical portion on the inner periphery of the engagement groove, with the conical portion located between the toothed portion and the opening, and with the conical portion having a conicity in a range of 8°-22°.

10. The dental implant as claimed in claim 9, with the conical portion including a surface, with the dental prosthesis further including an adhesion layer formed on the surface of the conical portion, with the adhesion layer of the dental prosthesis coupled to the adhesion layer of the abutment.

11. The dental implant as claimed in claim 10, with the adhesion layer also formed on a surface of the toothed portion.

* * * * *